United States Patent [19]

Kobayashi

[11] Patent Number: 5,095,501

[45] Date of Patent: Mar. 10, 1992

[54] X-RAY IMAGE-PICKUP APPARATUS

[75] Inventor: Tohru Kobayashi, Ootawara, Japan

[73] Assignee: Kabushiki Kaisha Toshiba, Kawasaki, Japan

[21] Appl. No.: 623,127

[22] Filed: Dec. 6, 1990

[30] Foreign Application Priority Data

Dec. 6, 1989 [JP] Japan .................................. 1-315491

[51] Int. Cl.$^5$ .............................................. H05G 1/02
[52] U.S. Cl. ..................... 378/196; 378/195; 378/197; 378/198
[58] Field of Search ........ 378/167, 189, 193, 195-198, 378/208

[56] References Cited

U.S. PATENT DOCUMENTS

| 3,549,885 | 12/1970 | Andersson | 375/193 |
| 3,803,418 | 4/1974 | Holstrom | 378/196 |
| 4,358,856 | 11/1982 | Stivender | 378/167 |
| 4,426,725 | 1/1984 | Grady | 378/196 |
| 4,741,015 | 4/1988 | Charrier | 378/197 |
| 4,884,293 | 11/1989 | Koyama | 378/196 |
| 4,961,214 | 10/1990 | Van Endschot et al. | 378/196 |

FOREIGN PATENT DOCUMENTS 2238706 2/1974 Fed. Rep. of Germany ...... 378/196

Primary Examiner—Janice A. Howell
Assistant Examiner—David P. Porta
Attorney, Agent, or Firm—Oblon, Spivak, McClelland, Maier & Neustadt

[57] ABSTRACT

An x-ray image-pickup apparatus comprises a base movable along a ceiling wall of a photographing room, a support having one end portion rotatably attached to the base, an arm rotatably and slidable attached to the other end portion of the support, and a pair of x-ray image-pickup systems arranged to be substantially included in an imaginary plane defined within the arm and designed to be capable of photographing a subject situated within the arm in two directions. The apparatus is suitable for a cephalo-cervical interventional angiography.

3 Claims, 8 Drawing Sheets

X-RAY IMAGE-PICKUP APPARATUS

BACKGROUND OF THE INVENTION

1. Field of the Invention

The present invention relates to an x-ray image-pickup apparatus suitable for a cephalo-cervical interventional angiography, which is known as one of the methods wherein diagnosis and treatment are simultaneously performed with use of a catheter.

2. Description of the Related Art

FIG. 1 shows schematically a typical example of this x-ray pickup apparatus. This apparatus is of a floor-installation type.

The apparatus comprises a floor stand 1 situated on a floor 10 at one side 10A of an inspection room; an C-arm 2 attached to the floor stand 1; an x-ray radiation system 3 attached to one end of the arm 2 and including an x-ray tube and a diaphragm device; an x-ray image detection system 4 attached to the other end of the arm 2 and including an image intensifier (I.I.), an optical system, a TV camera and a film changer (F.C.); and a bed 5 situated on the floor 10 at the other side 10B of the inspection room and located apart from the floor stand 1.

A subject 9 is placed on the bed 5 between the x-ray radiation system 3 and the x-ray image detection system 4 both attached to the C-arm 2. Fluoroscopy or image-pickup is effected through the opposite faces of the subject 9 located between the systems 3 and 4. The floor stand 1 is vertically movable in a direction of a double-headed arrow 6, the arm 2 is rotatable in a direction of a double-headed arrow 7, and the arm 2 is slidable in a direction of a double-headed arrow 8. By virtue of such multi-directional movements, fluoroscopy or image-pickup can be effected on the respective parts of the subject 9, with relatively high degrees of freedom of direction and distance.

There is a clinical demand that this type of x-ray image-pickup apparatus be able to perform fluoroscopy on, e.g. a part of the head, in two directions under the same temporal conditions. Typically, this demand occurs in a cephalo-cervical interventional angiography wherein diagnosis and treatment are simultaneously performed with use of a catheter.

In order to meet the clinical demand, the following apparatus structure is required. Two sets of the apparatuses each having the structure shown in FIG. 1 are provided, and these apparatuses are positioned in desired directions for fluoroscopy. In this case, a pair of C-arm 2, a pair of x-ray radiation systems 3, and a pair of x-ray image detection systems 4 must be arranged complicatedly around the subject 9. It is probable that the arms 2, systems 3 and 4 and subject 9 prevent each other's movement or collide with each other.

Under the situation, in order to satisfy the above clinical demand, additional staff members are necessary in addition to the provision of the above structure. Specifically, two sets of the apparatuses each having the structure shown in FIG. 1 are provided, in like manner, thereby realizing an apparatus structure for performing cephalo-cervical interventional angiography. This structure, however, is inadequate for performing the angiography. To perform the angiography, an operator, a diagnostic doctor, an anesthetist, nurses, engineers, etc. must attend near the bed 5. In this case, the jointly used two sets of apparatuses prevent each other's movement, and they may possibly collide with each other. In addition, since two bases 1 are provided near the head of the subject 9, it becomes difficult for the operator, etc. to access the head to be treated. The difficulty in anesthetizing the head is considerable.

SUMMARY OF THE INVENTION

An object of the present invention is to provide an x-ray image-pickup apparatus capable of x-ray photographing various parts of a subject in multiple modes, without narrowing the operation space of a doctor, etc.

Another object of the invention is to provide an x-ray image-pickup apparatus capable of performing an interventional angiography safely and conveniently.

According to an aspect of the invention, there is provided an x-ray image-pickup apparatus comprising:

a main body situated between a floor of a photographing room and one of the walls of the room excluding the floor, the main body having one end portion reaching said one of the walls of the room excluding the floor and the other end portion extending at a distance from the floor;

first image-pickup means, provided on said other end portion of the main body, for carrying out first x-ray imaging;

second image-pickup means, provided on said other end portion of the main body at a location different from the location where said first image-pickup means is provided, for carrying out second x-ray imaging; and a bed device situated at a predetermined location on the floor.

According to another aspect of the invention, there is provided an x-ray image pickup apparatus comprising:

a main body having one end portion attached to one of the walls of a photographing room excluding a floor;

first x-ray radiation means, provided on the other end portion of said main body, for radiating first x-rays in a first direction;

first x-ray detection means for detecting the first x-rays, situated to be substantially included, along with said first x-ray radiation means, in an imaginary plane defined at the other end portion of the main body;

second x-ray radiation means for radiating second x-rays in a second direction, the line of which intersects the line of the first direction in which the first x-rays are radiated, said second x-ray radiation means being situated to be substantially included, along with said first x-ray radiation means and said first x-ray detection means, in said imaginary plane defined at the other end portion of the main body;

second x-ray detection means for detecting the second x-rays, situated to be substantially included, along with said first x-ray radiation means, said first x-ray detection means and said second x-ray radiation means, in said imaginary plane defined at the other end portion of the main body; and a bed device situated at a predetermined location on the floor.

According to still another aspect of the invention, there is provided an x-ray image-pickup apparatus comprising:

a base member movable along one of the walls of a photographing room excluding a floor;

a support member having one end portion rotatably attached to said base member;

an arm holder member rotatably attached to the other end portion of the support member;

an arm member slidably disposed on the arm holder member;

first x-ray radiation means, provided on the arm member, for radiating first x-rays;

first x-ray detection means, provided on the arm member, for detecting the first x-rays, said first x-ray detection means being situated at a first distance from the first x-ray radiation means;

second x-ray radiation means for radiating second x-rays, provided on the arm member at a location different from the location where said first x-ray radiation means is provided;

second x-ray detection means for detecting the second x-rays, provided on the arm member at a location different from the location where said second x-ray detection means is provided and situated at a second distance from the second x-ray radiation means; and a bed device situated at a predetermined location on the floor.

According to still another aspect of the invention, there is provided an x-ray image-pickup apparatus comprising:

a base member movable along one of the walls of a photographing room excluding a floor;

a support member having one end portion rotatably attached to said base member;

an arm holder member rotatably attached to the other end portion of the support member;

an arm member slidably disposed on the arm holder member;

first x-ray radiation means, provided on the arm member, for radiating first x-rays;

first x-ray detection means, provided on the arm member, for detecting the first x-rays, said first x-ray detection means being situated at a first distance from the first x-ray radiation means;

second x-ray radiation means for radiating second x-rays, provided on the arm member at a location different from the location where said first x-ray radiation means is provided;

second x-ray detection means for detecting the second x-rays, provided on the arm member at a location different from the location where said second x-ray detection means is provided and situated at a second distance from the second x-ray radiation means;

a bed device situated at a predetermined location on the floor; and a control system having storage means for storing data relating to inside dimensions of said room, and/or data relating to a minimum allowable distance between the bed device on one hand and the base member, the support member, the arm holder member and the arm member on the other hand, and, on the basis of the data stored in the storage means, controlling at least the movement of the base member, the rotation of the support member, the rotation of the arm holder member and the sliding movement of the arm member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

DETAILED DESCRIPTION OF THE PREFERRED EMBODIMENTS

An x-ray image pickup apparatus according to an embodiment of the present invention will now be described.

Figure 1:
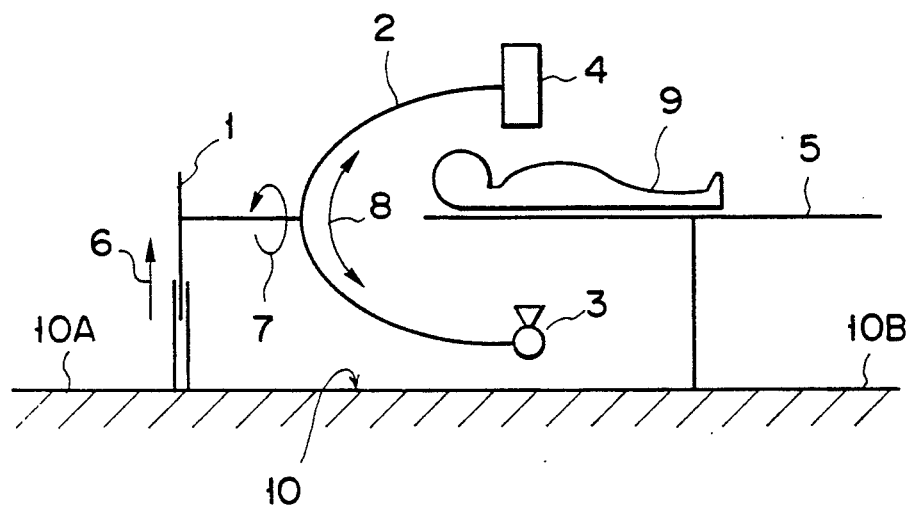
FIG. 1 schematically shows a typical example of an x-ray image-pickup apparatus.
Figure 2:
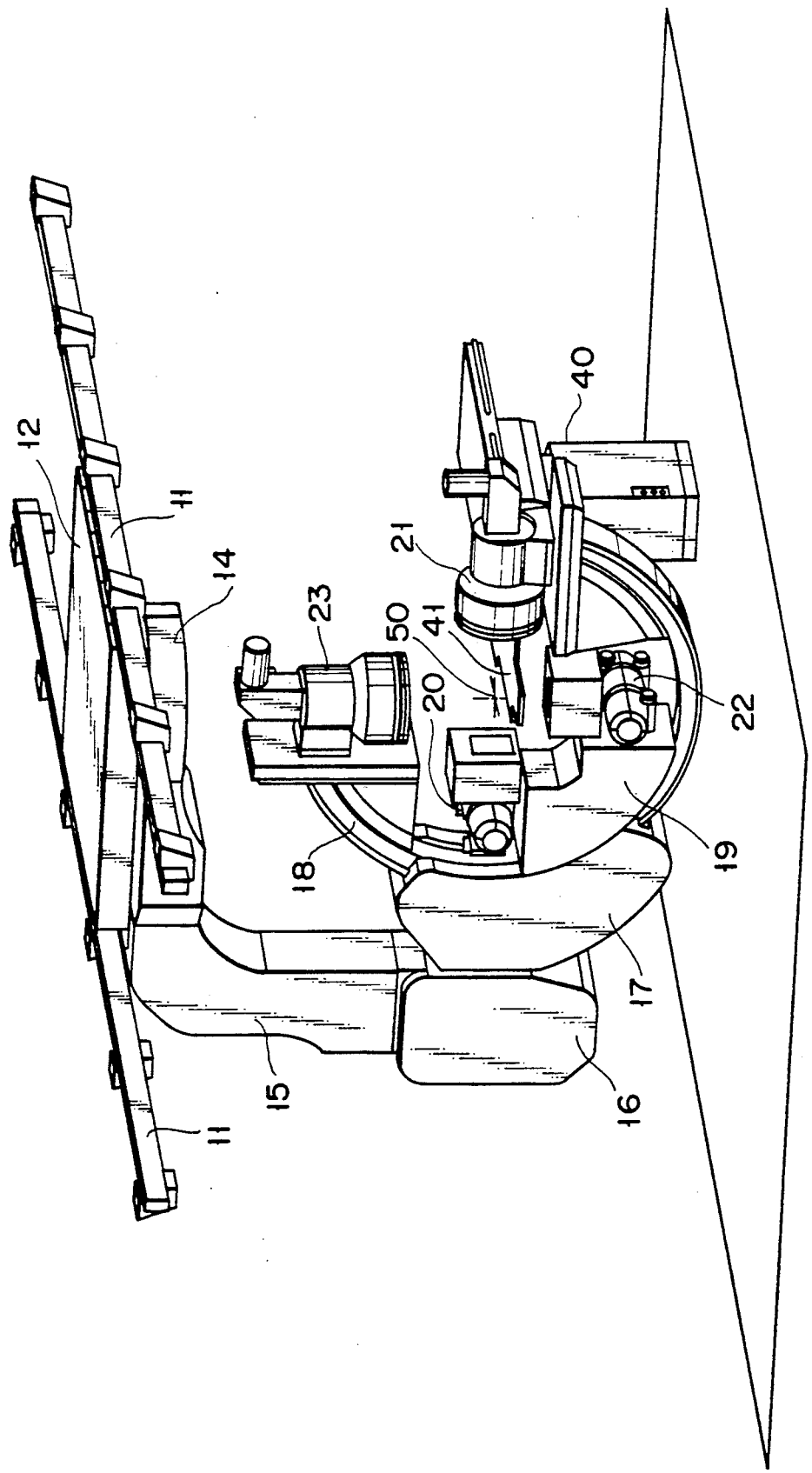
FIG. 2 is a perspective view showing mechanical elements of an x-ray image pickup apparatus according to an embodiment of the present invention.
Figure 3A:
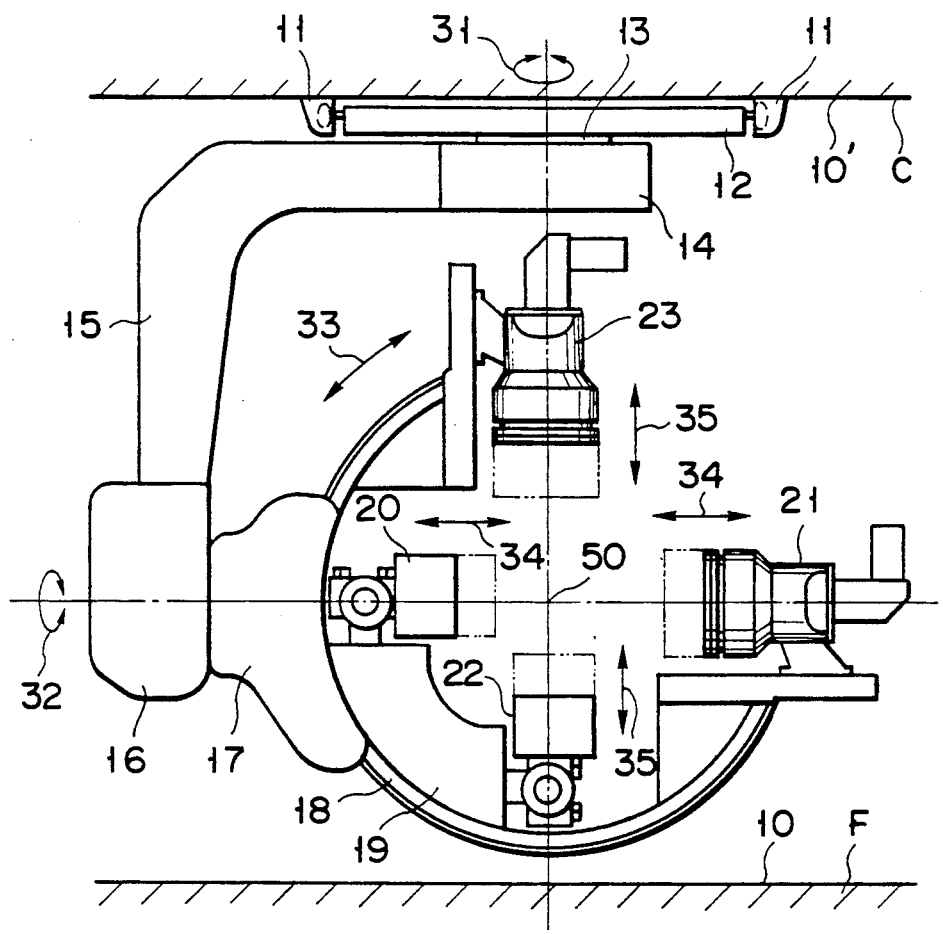
FIG. 3A is a front view of the apparatus shown in FIG. 2.
Figure 3B:
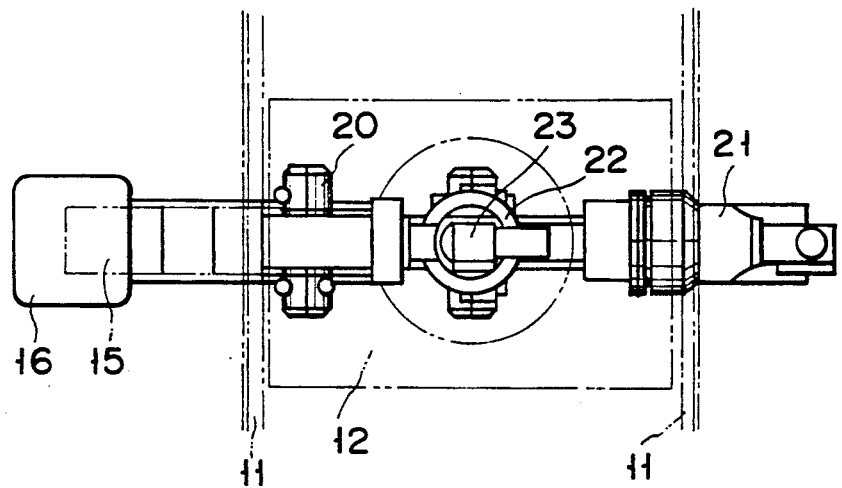
FIG. 3B is a plan view of the apparatus shown in FIG. 2, as viewed from the ceiling (or from the floor)

As shown in FIGS. 2, 3A and 3B, a pair of ceiling rails 11 are arranged, with a distance therebetween, on a ceiling wall 10', which is one of the walls of a photographing room excluding a floor 10. A ceiling base 12 is movably mounted on the ceiling rail 11. The ceiling base 12 has a shaft 13. An upper support frame 14 is mounted on the shaft 13 so as to be rotatable in a direction denoted by a double-headed arrow 31. One end portion of an L-shaped arm 15 is attached to the upper support frame 14.

The other end portion of the support 15 is attached to a G-ring rotation drive unit 16. A shaft (not shown), which is rotatable in a direction denoted by a double-headed arrow 32, is disposed within the G-ring rotation drive unit 16 and is connected to an arm base 17.

A ring 18 slidable in a direction indicated by a double-headed arrow 33 is attached to the arm base 17. The ring 18 has an arcuate form corresponding to 3/4 of a circle. The ring 18 is known as a G-shaped ring or half ring. First x-ray radiation means or an x-ray source 20, which is slidable in a direction indicated by an arrow 34, and second x-ray radiation means or an x-ray source 22, which is slidable in a direction indicated by an arrow 35, are disposed on the inside of the ring 18. First x-ray detector 21 slidable in the direction of arrow 34 and second x-ray detector 23 slidable in the direction of arrow 35 are disposed at both end portions of the ring 18. The first x-ray source 20, first x-ray detector 21, second x-ray source 22 and second x-ray detector 23 are arranged on the ring 18 such that a line connecting the center of the first x-ray source 20 and the center of the first x-ray detector 21 and a line connecting the center of the second x-ray source 22 and the center of the second x-ray detector 23 intersect at right angles. Each of the first and second x-ray sources 20 and 22 comprises an x-ray tube, a diaphragm device, etc. Each of the first and second x-ray detectors 21 and 23 comprises an image intensifier (I.I.), an optical system, a TV camera, etc.

Figure 3C:
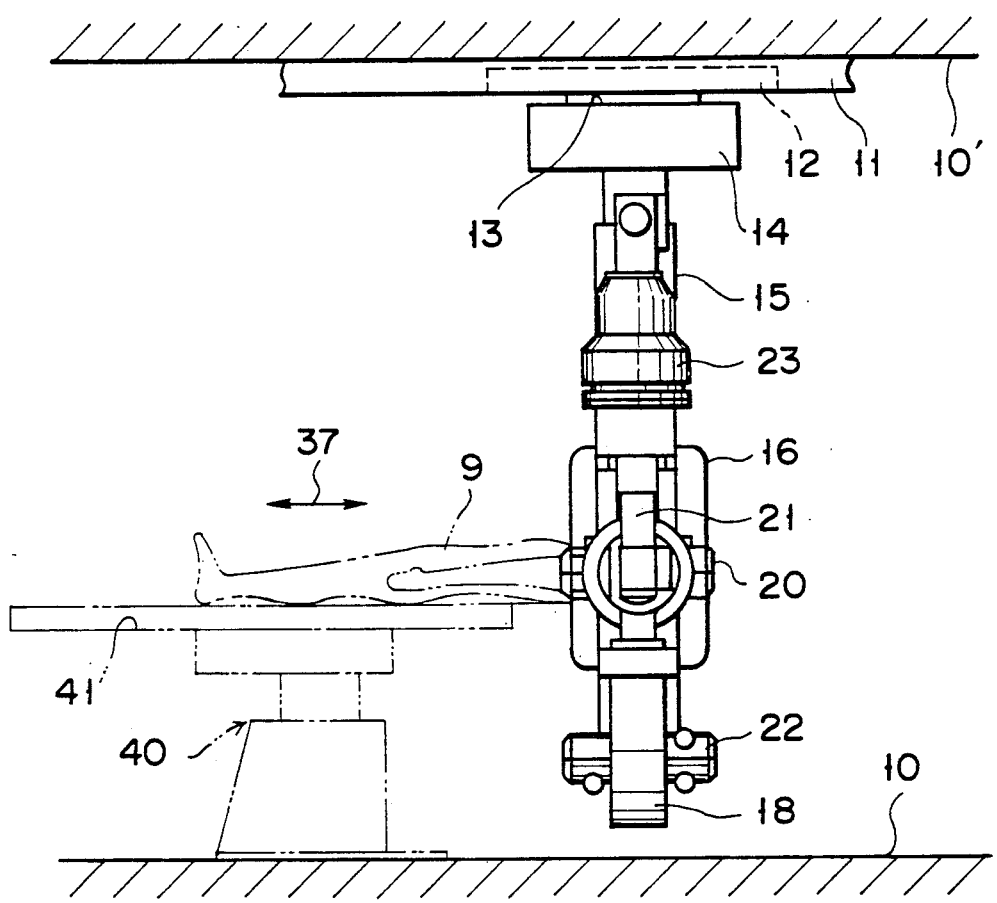
FIG. 3C is a side view of the apparatus shown in FIG. 2.

As is shown in FIG. 3C, a bed 40 having a top plate 41, which is movable in a direction of a double-headed arrow 37, is installed on the floor 10. A subject is placed on the plate 41, and the plate 41 is moved so that the location of the subject 9 may coincide with the center 50 within the ring 18.

Figure 4:
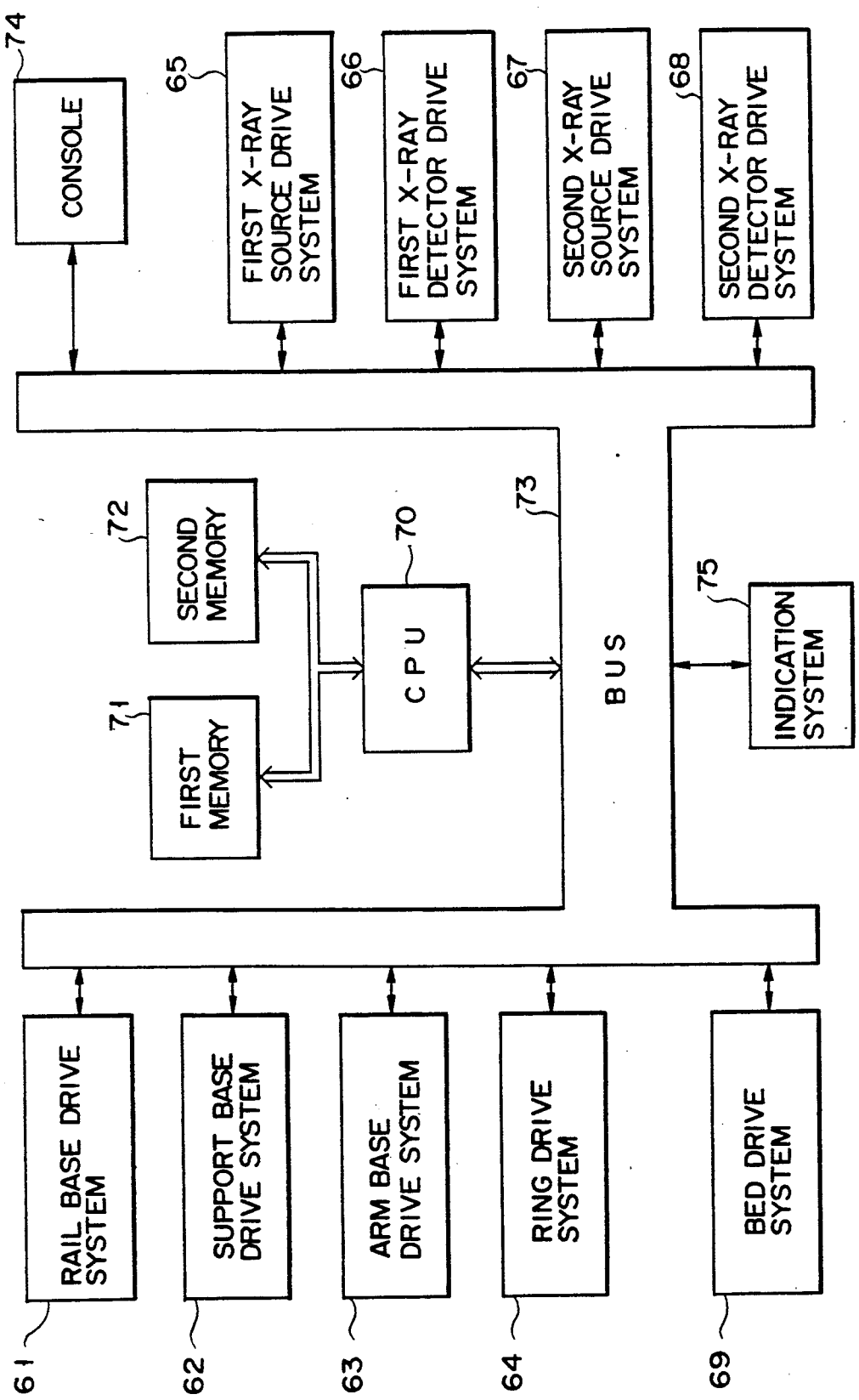
FIG. 4 is a block diagram showing electric elements for driving the mechanical elements of the apparatus shown in FIG. 2.

FIG. 4 shows a drive system for driving the respective elements. The linear movement of the ceiling base 12 along the rails 11 is controlled by a rail base drive system 61. The rotational movement of the support frame 14 in the direction of arrow 31 is controlled by a support base drive system 62. The rotational movement of the arm base 17 in the direction of arrow 32 is controlled by an arm base drive system 63. The sliding movement of the ring 18 in the direction of arrow 33 is controlled by a ring drive system 64. The sliding movement of the first x-ray source 20 in the direction of arrow 34 is controlled by a first x-ray source drive system 65. The sliding movement of the first x-ray detector 21 in the direction of arrow 34 is controlled by a first x-ray detector drive system 66. The sliding movement of the second x-ray source 22 in the direction of arrow 35 is controlled by a second x-ray source drive system 67. The sliding movement of the second x-ray detector 23 in the direction of arrow 35 is controlled by a second x-ray detector drive system 68. The elevation of the bed 40 and the movement of the top plate 41 in the direction of arrow 37 are controlled by a bed drive system 69. Each drive system comprises a motor driver, a motor, a gear, an encoder, an interface, etc. In addition to the above-mentioned drive systems, the control system of the x-ray image pickup apparatus includes a CPU 70; a first memory 71 for storing inside dimension data relating to the photographing room; a second memory 72 for storing data relating to a minimum distance to which the respective elements can be approached to the subject 9; a bus 73 through which data can be transmitted between the respective drive systems and the CPU 70, etc.; a console 74 for generating an operator's commands; and an indication system 75 for providing information, in the form of sound information or visual information, relating to the condition of the apparatus to an operator, a doctor, etc.

The operator can operate the console 72 of the control system, so that the first x-ray source 20 and first x-ray detector 21, which are slidable in the direction of arrow 34, may be driven in synchronism with, or independently of, the second x-ray source 22 and second x-ray detector 23. Accordingly, an SID (x-ray source - image intensifier (I.I.) distance) and a geometrical enlargement ratio can be varied with respect to the first x-ray source 20 and first x-ray detector 21 on the one hand and the second x-ray source 22 and second x-ray detector 23 on the other, synchronously or independently. For example, regarding both systems of x-ray sources and detectors, the geometrical enlargement ratio can be varied while the SID is kept constant, or the SID and geometrical enlargement ratio can be varied successively.

Figure 5:
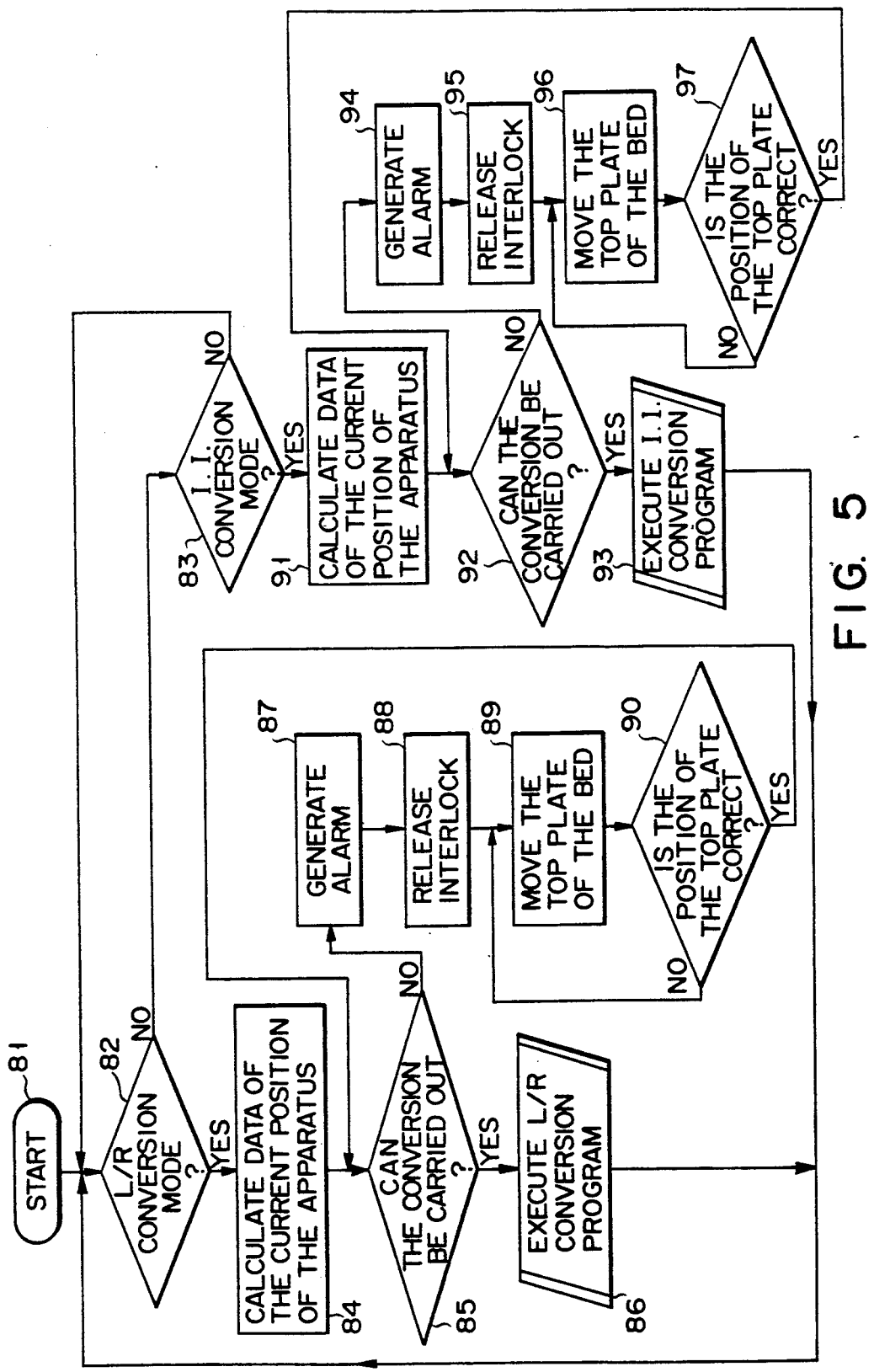
FIG. 5 is a flowchart for illustrating the operation of the mechanical elements of the apparatus of FIG. 2.
Figure 6A:
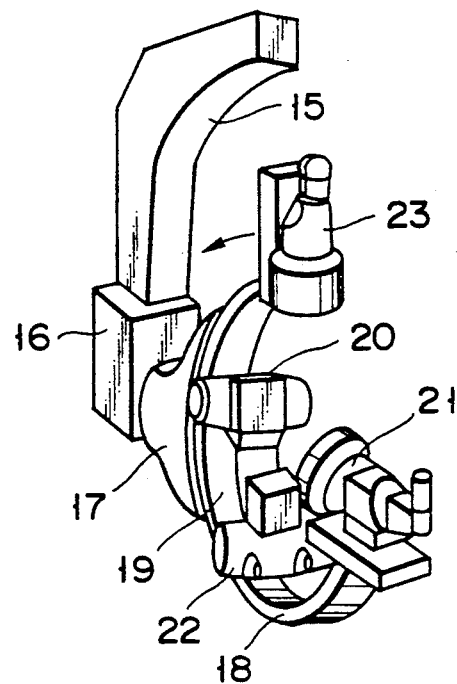
FIGS. 6A, 6B, 6C and 6D are schematic perspective views for illustrating the rotational motion of a support and the sliding motion of an arm in the apparatus of FIG. 2.
Figure 6B:
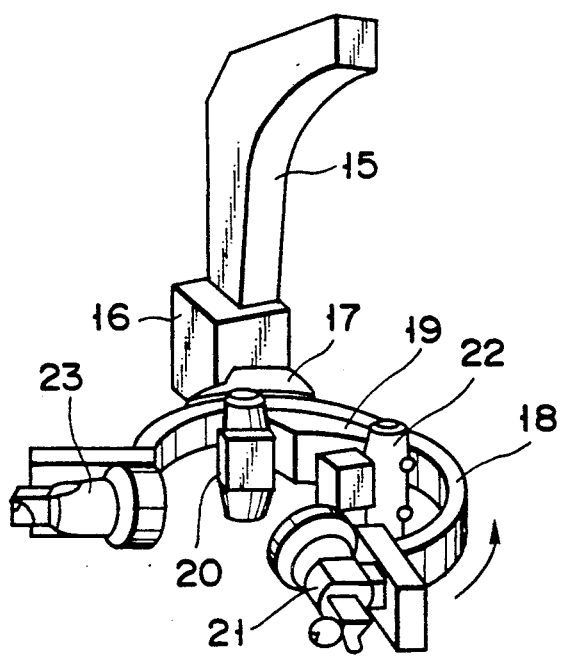
Figure 6C:
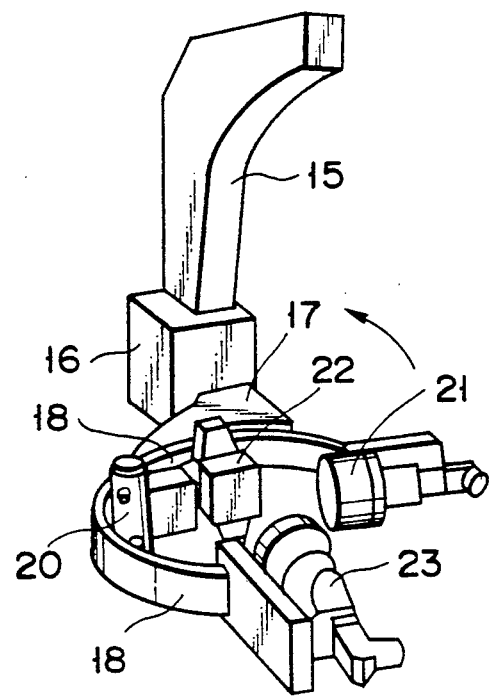
Figure 6D:
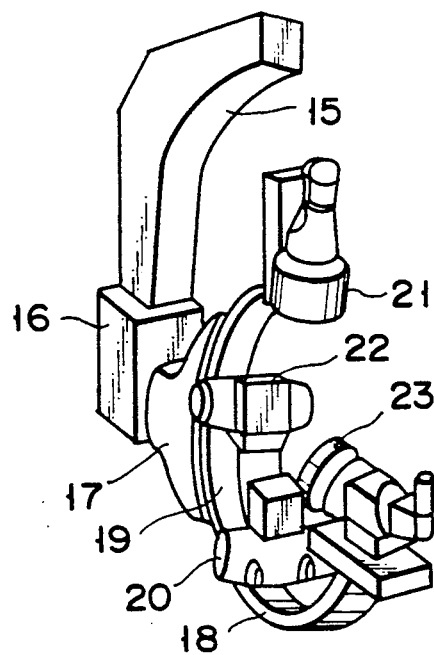

FIG. 5 illustrates the operation of the x-ray image pickup apparatus. The apparatus can operate in two modes. In one mode, the support 15, ring 18, etc. are moved from the left side to the right side of the bed 40 (or from the right side to the left side) (an L/R conversion mode or an off-set position conversion mode). In the other mode, while the position of the ring 18 is unchanged, the second x-ray source 22 is brought to the location of the first x-ray source 20 and the second x-ray detector 23 is brought to the location of the first x-ray detector 21 (an I.I. conversion mode or an x-ray tube conversion mode). The control programs for both modes are stored in the CPU 70 and are executed upon the operation of the console 74 by the operator. The L/R conversion mode is carried out in a step 82 and steps 84 to 90, while the I.I. conversion mode is carried out in a step 83 and steps 91 to 97. The I.I. conversion mode is a conversion between a large-diameter I.I. and a small-diameter I.I., and the x-ray tube conversion mode includes a conversion between a large-capacitance x-ray tube and a small-capacitance x-ray tube and a conversion between a stereo x-ray tube and a conventional x-ray tube.

The operator operates the console 74 to start the programs (step 81). When the operator selects the L/R conversion mode, steps 82 and steps 84 to 90 are executed. The L/R conversion mode and I.I. conversion mode are determined in steps 82 and 83. When the L/R conversion mode is selected in step 82, the data of the current position of the apparatus is calculated (step 84). The current position data can be obtained from the encoders, etc. included in the respective drive systems shown in FIG. 4. The current position data is stored in storage means in the CPU 70. In step 85, the CPU 70 compares the current position data with the inside dimension data stored in the first memory 71, which relates to the inside dimensions of the photographing room, and with the data stored in the second memory 72 which relates to the minimum allowable distance between the subject 9 and the respective elements of the apparatus. For example, when it is determined that the apparatus is positioned such that the minimum allowable distance between the subject 9 and the respective elements is kept, the L/R conversion program is executed in step 86. On the other hand, if the minimum allowable distance is not kept, the indication system 75 generates an alarm to the operator (in step 87). Responding to the alarm, the operator releases an interlock in step 88 and retreats the top plate 41 in step 89. In step 90, it is determined whether the top plate 41 is located in an allowable positional range. If YES in step 90, the control routine returns to step 85 and the L/R conversion program is executed in step 86. Thus, the respective elements are driven.

On the other hand, when the I.I. conversion mode is selected in steps 82 and 83, the data of the current position of the apparatus is calculated (step 91). The current position data can be obtained from the encoders, etc. included in the respective drive systems shown in FIG. 4. The current position data is stored in storage means in the CPU 70. In step 92, the CPU 70 compares the current position data with the inside dimension data stored in the first memory 71, which relates to the inside dimensions of the photographing room, and with the data stored in the second memory 72 which relates to the minimum allowable distance between the subject 9 and the respective elements of the apparatus. For example, when it is determined that the apparatus is positioned such that the minimum allowable distance between the subject 9 and the respective elements is kept, the I.I. conversion program is executed in step 93, and the respective elements are driven. On the other hand, if the minimum allowable distance is not kept, the indication system 75 generates an alarm to the operator (in step 94). Responding to the alarm, the operator releases an interlock in step 95 and retreats the top plate 41 in step 96. In step 97, it is determined whether the top plate 41 is located in an allowable positional range. If YES in step 97, the control routine returns to step 92 and the L/R conversion program is executed in step 93. Thus, the respective elements are driven. The operation in the I.I. conversion mode is illustrated in FIG. 6 in the order from FIG. 6A to FIG. 6B, to FIG. 6C and to FIG. 6D.

As is shown in FIGS. 6A to 6D, the system of first x-ray source 20 and x-ray detector 21 and the system of second x-ray source 22 and x-ray detector 23 can be approached to the subject 9 individually. Thus, x-ray images of a desired part can be obtained by both systems in multi-directions. In particular, when it is required from clinical aspects to carry out fluoroscopy on the side faces of the head from the right and left directions under the same conditions by rotating the apparatus in the direction of arrow 31, such fluoroscopy can be performed easily with use of a single apparatus, without interference of the respective elements. The rotational movements and sliding movements of the respective elements are suitable, in particular, for a cephalo-cervical interventional angiography (wherein diagnosis and treatment are simultaneously carried out with use of catheter).

Furthermore, since the base 12 or the apparatus can be moved along the ceiling rail 11, the apparatus can be approached to, or retreated from, the subject 9 without moving the subject 9 in which a catheter is inserted. The positioning of the apparatus is easy and safe. When the respective elements of the apparatus interfere with the subject in positional relationship, the elements are first moved, without moving the subject. This is a principle applicable to this type of medical equipment.

The above description has been directed mainly to the mechanical structure of the apparatus. As has been described above, according to the apparatus of this invention, the inside dimension data of the photographing room and the data relating to the minimum allowable distance between the subject and the apparatus elements are stored in advance in the console 74 or the control system. When the apparatus is driven and the elements are moved excessively close to the inside walls of the room or the subject, the stored data is collated to operate safety mechanisms, for example, for driving a limiter or an interlock or generating an alarm. Thus, the safety of the subject 9 can be ensured, and the damage to the apparatus or inspection room can be prevented.

Therefore, the present invention can provide an x-ray image-pickup apparatus capable of performing x-ray image-pickup on a subject with high degrees of freedom.

Additional advantages and modifications will readily occur to those skilled in the art. Therefore, the invention in its broader aspects is not limited to the specific details, and representative devices, shown and described herein. Accordingly, various modifications may be without departing from the spirit or scope of the general inventive concept as defined by the appended claims and their equivalents.

What is claimed is:

1. An x-ray image-pickup apparatus comprising:
   a base member movable along one of the walls of a photographing room excluding a floor;
   a support member having one end portion rotatably attached to said base member;
   an arm holder member rotatably attached to the other end portion of the support member;
   an arm member slidably disposed on the arm holder member;
   first x-ray radiation means, provided on the arm member, for radiating first x-rays;
   first x-ray detection means, provided on the arm member, for detecting the first x-rays, said first x-ray detection means being situated at a first distance from the first x-ray radiation means;
   second x-ray radiation means for radiating second x-rays, provided on the arm member at a location different from the location where said first x-ray radiation means is provided;
   second x-ray detection means for detecting the second x-rays, provided on the arm member at a location different from the location where said second x-ray detection means is provided and situated at a second distance from the second x-ray radiation means;
   a bed device situated at a predetermined location on the floor; and
   a control system having storage means for storing data relating to inside dimensions of said room, and/or data relating to a minimum allowable distance between the bed device on one hand and the base member, the support member, the arm holder member and the arm member on the other hand, and, on the basis of the data stored in the storage means, controlling at least the movement of the base member, the rotation of the support member, the rotation of the arm holder member and the sliding movement of the arm member.

2. The apparatus according to claim 1, wherein said control system has a control mode in which the base member, the support member, the arm holder member and the arm member are driven so as to change the position of the arm member from one side of the bed device to the other side of the bed device.

3. The apparatus according to claim 1, wherein said control system has a control mode in which the base member, the support member, the arm holder member and the arm member are driven so as to change the position of the first x-ray radiation means and the first x-ray detection means in the photographing room to the position of the second x-ray radiation means and the second x-ray detection means in the room.

* * * * *